United States Patent
Yatvin (10) Patent No.: US 7,316,818 B2
(45) Date of Patent: *Jan. 8, 2008

(54) LIPOSOME DRUG DELIVERY OF POLYCYCLIC, AROMATIC, ANTIOXIDANT OR ANTI-INFLAMMATORY COMPOUNDS

(75) Inventor: Milton Yatvin, Portland, OR (US)

(73) Assignee: Oradel Medical Ltd. (IL)

(*) Notice: Subject to any disclaimer, the term of this patent is extended or adjusted under 35 U.S.C. 154(b) by 0 days.

This patent is subject to a terminal disclaimer.

(21) Appl. No.: 10/999,896

(22) Filed: Nov. 30, 2004

(65) Prior Publication Data

US 2005/0152978 A1 Jul. 14, 2005

Related U.S. Application Data

(63) Continuation of application No. 10/339,877, filed on Jan. 9, 2003, now Pat. No. 6,824,790.

(60) Provisional application No. 60/347,759, filed on Jan. 9, 2002.

(51) Int. Cl.
*A61K 9/127* (2006.01)
*A61K 9/14* (2006.01)
*A61K 9/30* (2006.01)
*A61K 9/56* (2006.01)

(52) U.S. Cl. ............ 424/450; 424/458; 424/459; 424/462; 424/468; 424/470; 424/474; 424/482; 424/489; 424/497

(58) Field of Classification Search ........ 424/450–451, 424/458–464, 468–470, 474–482, 489–502
See application file for complete search history.

(56) References Cited

U.S. PATENT DOCUMENTS

| 4,302,440 | A | * | 11/1981 | John et al. ............... 424/480 |
| 4,615,885 | A | | 10/1986 | Nakagame et al. |
| 4,687,762 | A | | 8/1987 | Fukushima et al. |
| 4,744,989 | A | | 5/1988 | Payne et al. |
| 4,857,337 | A | * | 8/1989 | Miller et al. ............. 424/480 |
| 4,921,757 | A | | 5/1990 | Wheatley et al. |
| 4,963,526 | A | | 10/1990 | Ecanow et al. |
| 5,004,611 | A | | 4/1991 | Leigh |
| 5,043,165 | A | | 8/1991 | Radhakrishnan |
| 5,053,217 | A | | 10/1991 | Lehigh |

(Continued)

FOREIGN PATENT DOCUMENTS

EP 350287 1/1990

(Continued)

OTHER PUBLICATIONS

Payne et al., "Prolipsomes: A Novel Solution to an Old Problem, *Journal of Pharmaceutical Sciences*", 75(4)325-6 (Apr. 1, 1986).

(Continued)

*Primary Examiner*—Gollamudi S. Kishore
(74) *Attorney, Agent, or Firm*—McDonnell Boehnen Hulbert & Berghoff (57) ABSTRACT

This invention comprises pharmaceutical compositions for administering a polycyclic, aromatic, antioxidant or anti-inflammatory compound to an animal. Particularly provided are proliposomal compositions that are advantageously used to deliver polycyclic, aromatic, antioxidant or anti-inflammatory compounds to the gastrointestinal tract after oral administration.

33 Claims, 7 Drawing Sheets

DSPC = DISTEARYLPHOSPHATIDYLCHOLINE
POS = STEARYLAMINE
CHOL = CHOLESTEROL
NEG = DICETYLPHOSPHATE
NEU = NEUTRAL LIPID = ?

U.S. PATENT DOCUMENTS

| | | | |
|---|---|---|---|
| 5,141,674 | A | 8/1992 | Leigh |
| 5,223,263 | A | 6/1993 | Hostetler et al. |
| 5,466,468 | A | 11/1995 | Schneider et al. |
| 5,484,809 | A | 1/1996 | Hostetler et al. |
| 5,580,571 | A | 12/1996 | Hostetler et al. |
| 5,595,756 | A * | 1/1997 | Bally et al. ............ 424/450 |
| 5,610,163 | A | 3/1997 | Banholzer et al. |
| 5,626,869 | A | 5/1997 | Nyqvist et al. |
| 5,635,206 | A | 6/1997 | Ganter et al. |
| 5,654,314 | A | 8/1997 | Banholzer et al. |
| 5,665,379 | A | 9/1997 | Herslof |
| 5,738,868 | A | 4/1998 | Shinkarenko |
| 5,744,461 | A | 4/1998 | Hostetler |
| 5,744,592 | A | 4/1998 | Hostetler et al. |
| 5,756,116 | A | 5/1998 | Hostetler et al. |
| 5,762,904 | A | 6/1998 | Okada et al. |
| 5,770,738 | A | 6/1998 | Banholzer et al. |
| 5,843,509 | A | 12/1998 | Calvo Salve et al. |
| 5,955,451 | A | 9/1999 | Lichtenberger et al. |
| 5,958,450 | A | 9/1999 | Tashiro et al. |
| 6,015,576 | A | 1/2000 | See et al. |
| 6,060,082 | A | 5/2000 | Chen et al. |
| 6,117,449 | A | 9/2000 | See et al. |
| 6,207,185 | B1 | 3/2001 | See et al. |
| 6,207,190 | B1 | 3/2001 | Richardson et al. |
| 6,231,888 | B1 | 5/2001 | Lerner et al. |
| 6,824,790 | B2 * | 11/2004 | Yatvin ............ 424/450 |

FOREIGN PATENT DOCUMENTS

| | | | |
|---|---|---|---|
| EP | 0 736 299 A | | 10/1996 |
| EP | 0855 179 A | | 7/1998 |
| EP | 0855179 A2 * | | 7/1998 |
| FR | 2 581 543 A | | 7/1986 |
| WO | WO 8902733 | | 4/1989 |
| WO | WO94 28876 A | | 12/1994 |
| WO | WO 9503035 | | 2/1995 |
| WO | WO97 12580 A | | 4/1997 |
| WO | WO 9300910 | | 1/1998 |
| WO | WO 00 28989 A | | 5/2000 |
| WO | WO 02 13782 A | | 2/2002 |

OTHER PUBLICATIONS

Kumar et al., Formulation characterization an in vitro release of Glyburide from Proliposomal beads STN Database accession No. 2001082693 XP002184270.

Katare et al., "Proliposomes of Indomethacin for Oral Administration", Journal of Microencapsulation, Taylor and Francis Inc. London, GB, 8(1)1-7 (1991).

Katare et al., "Effecvescent Granule Based Proliposomes of Ibuprofen", Journal of Microencapsulation, *Taylor and Fransis Inc. London, GB,* 7(4) 355-62 (Oct. 1990).

Oku N. et al., "Effect of Freeze-Thawing on Phospholipid/Surfactant Mixed Bilayers" *Chemical and Pharmaceutical Bulletin, Pharmaceutical Society of Japan. Tokyo, JP* 44(10)1928-30 (Oct. 1, 1996).

Alvarez-Dominquez et al., "Role of Complement Component C1q in Phagoctosis of Listeria monocytogenes by Murine Macrophage-Like Lines", *Infect Immun.* 61:3664-72 (1993).

Bignami et al., "N-(-4'-Hydroxyphenylacetyl) palytoxin: A Palytoxin Prodrug That Can Be Activated by a Monoclonal Antibody-Penicellin G Amidase Conjugate", 1992 *Cancer Res* 52:5759-64 (1992).

Embretson et al., "Massive covert infection of helper T lymphohocytes and macrophages by HIV during the incubation period of AIDS", *Nature* 362:359-62 (1993).

Gregoriadis et al., "Engineering liposomes for drug delivery: progress and problems", *Trends in Biotechnology* 13:527-37 (1995).

Kanno et al., "Aleutian Milk Disease Parvovirus Infection of Mink Peritoneal Macrophages and Human Macrophage Cell Lines", *J. Virol.* 67:2075-82 (1993).

Kanno et al., "Infection of Aleutian Mink Disease Parvovirus Transcripts in Macrophages of Infected Adult Mink". *J. Virol* 66:5305-5312 (1992).

Kulkarni et al. "Protamine-induced Aggregation of Unilamellar Liposomes" Pharmaceutical Science 1:359-362 (1995).

Maciejewski et al., "Infection of Mononucleated Phagocytes with Human Cytomegalovirus", *Virol* 195:327-336 (1993).

Manusama et al., "Tumor Necoris Factor-Alpha in Isolated Perfusion Systems in the Treatment of Cancer: The Rotterdam Preclinical-Clinical Program", Semin. Surg. Oncol. 14:232-237 (1998).

Meltzer & Gendelma et al., "Mononuclear Phagocytes as Targets, Tissue Reservoirs, and immunoregulatory Cells in Human Immunodeficiency Virus Disease", Curr. Top. Microbiol Immunol. 181:239-63 (1992).

Mickisch et al., "Gene Therapy on Renal-Cell Carcinoma: magic bullet of tragic insanity", World J. Urology 13:178-185 (1995).

Rahman et al., "Differential Uptake of Liposomes Varying in Size and Lipid Composition by Parentchymal and Kupffer Cells of Mouse Liver", 31:2061-71 (1982).

Sierra-Honigman et al., "Borna disease virus in peripheral blood mononuclear and bone marrow cells of neonatally and chronically infected rats", J. Neuroimmunal 45:31-36 (1993).

Storm and Crommetin "Colloidal Systems for Tumor Targeting" Hybridoma 16(1) 1997.

Sturgill-Koszycki et al., "Lack of Acidification in Mycobacterium Phagosomes Produced by Exclusion of the Vesicular Proton-ATPase", Science 263:678-681 (1994).

Yang et al., "Gene Therapy for Central Nervous System Injury: The Use of Cationic Liposomes: An Invited Review", J. Neurotrauma 14:281-297 (1997).

* cited by examiner

LIPOSOME DRUG DELIVERY OF POLYCYCLIC, AROMATIC, ANTIOXIDANT OR ANTI-INFLAMMATORY COMPOUNDS

This application is a continuation of U.S. Ser. No. 10/339,877, filed Jan. 9, 2003, now U.S. Pat. No. 6,824,790, issued Nov. 30, 2004, which claims priority to U.S. Provisional Application, Ser. No. 60/347,759, filed Jan. 9, 2002, the disclosure of which is explicitly incorporated by reference herein.

BACKGROUND OF THE INVENTION

1. Field of the Invention

This invention relates to delivery of polycyclic, aromatic, antioxidant or anti-inflammatory compounds to a biological organism. In particular, the invention relates to liposomes and formulations of drugs, nutrients and other compounds into liposomes to improve or effect delivery of such beneficial compounds to cells and tissues in an organism. Specifically, the invention provides such liposome compositions of polycyclic, aromatic, antioxidant or anti-inflammatory compounds in formulations advantageously administered orally to an animal.

2. Background of the Related Art

Cardiovascular disease (including atherosclerosis, myocardial infarction, ischemia, stroke, pulmonary embolism and other thrombotic diseases) and cancer are major causes of mortality in the U.S., being responsible for up to two-thirds of all deaths per annum. Despite advances in preventative medicine, diet, exercise, diagnostics and therapeutic approaches that have increased the average lifespan of U.S. citizens and reduced the number of premature deaths, these diseases ultimately are no less responsible for mortality than they were a generation ago.

Certain plant-derived compounds have been recognized as being beneficial both as anticancer and anticardiovascular disease agents. This class of compounds is generally recognized to include polycyclic, aromatic compounds having antioxidant or anti-inflammatory activity, and include the flavonoids (such as flavone, quercetin and chrysin) and derivatives of stilbenes, such as resveratrol. The effects of these compounds as anticancer and anticardiovascular disease agents are both anecdotal and subject to modem scientific scrutiny. One example of anecdotal evidence for the beneficial effects of these compounds is with regard to what has been termed "French paradox." The paradox is that although the French diet is high in nutrients (such as cholesterol and saturated fats) that have been associated with a risk of arteriosclerosis and cardiovascular disease, French citizens have less cardiovascular disease than their counterparts in other Western countries. The purported reason for this result is that French citizens also consume more red wine that other Western country citizens, and red wine is high (5-50 parts per million) in one polycyclic, aromatic antioxidant compound, resveratrol (Siemann & Creasy, 1992, *Am. J. Enol. Vitic.* 43: 49-52; Kopp et al., 1998, *Eur. J. Endocrinol.* 138: 619-620). Resveratrol is also a component of a traditional oriental medicine, Ko-jo-kon, used to treat ailments of the heart, blood vessels and liver. Soleas et al., 1997, *Clin. Biochem.* 30: 91-113.

Resveratrol is found in red wine due to its presence in grape skin, and is thought to be a phytoalexin that provides protection against fungi. Celotti et al., 1996, *J. Chromatog.* 730: 47-52. It is also found (at much lower concentrations) in eucalyptus, spruce, lily, mulberry and peanuts.

Resveratrol has also been the subject of several scientific studies. The Copenhagen Heart Study (1995) showed that the relative risk of mortality from coronary artery disease was reduced by 20% when red wine was consumed once a month, by 30% when red wine was consumed once or twice weekly, and by 40% when red wine was consumed 3-5 times per weeks. Other researchers investigated the physiologic basis for these results. Pendurthi et al. (1999) showed that resveratrol, dose-dependently, inhibited transcription and expression of tissue factor in endothelial cells. *Arteriosche-rosis Thrombosis and Vascular Biol.* 19: 419-426. Resveratrol has been shown to have antioxidant (Chanvitayapongs et al., 1997, *Neuroreport* 8: 1499-1502; Belguendouz et al., 1998, *Biochem. Pharmacol.* 55: 811-816; Frankel et al., 1993, *Lancet* 341: 1103-1104), platelet aggregation inhibiting (Bertelli et al., 1996, *Drugs Exp. Clin. Res.* 22: 61-63; Rotondo et al., 1998, *Brit. J. Pharmacol.* 123: 1691-1699) and vasodilating (Chen et al., 1996, *Gen. Pharm.* 27: 363-366) properties. Resveratrol has also been shown to have cancer chemopreventative properties (Jang et al., 1997, *Science* 275: 218-220), putatively by inhibiting COX-1 and COX-2 and tumor promotion thereby (Subbaramaiah et al., *J Biol. Chem.* 273: 21875-21882; Clement et al., 1998, *Blood* 92: 996-1002; Fontecave et al., 1998, *FEBS Lett.* 421: 277-279).

As a consequence, the World Health Organization estimates that coronary artery disease could be reduced by up to 40% if resveratrol or resveratrol-containing foods were consumed in proper amounts.

Chrysin (5,7-dihydroxyflavone) is a naturally-occurring flavone found in passion flower (*Passiflora coerulea*) extracts. Chrysin has activity as an anxiolytic agent (Wolfman et al., 1994, *Pharmacol Biochem. Behav.* 47: 1-4; Paladini et al., 1999, *J. Pharm. Pharmacol.* 51: 519-526), an anticonvulsant (Medina et al., 1990, *Biochem. Pharmacol.* 40: 2227-31), an agent that reverses P-glycoprotein mediated multidrug resistance in human cancer cells (Barron et al., $2^{nd}$ International Electronic Conference on Synthetic Organic Chemistry (ECSOC-2), Sep. 1-20, 1998, www.m-dpi.org/ecsoc), and as a protein kinase inhibitor (Hagiwara et al., 1988, *Biochem. Pharmacol.* 37: 2987-2992). Myocardial infarction risk in elderly men is decreased by chrysin (Hertog et al., 1993, *Lancet* 342: 1007-1011). Chrysin is believed to act by inhibiting aromatase, an enzyme responsible, inter alia, for converting testosterone to estrogen.

Quercetin (3,3',4',5,7-pentahydroxyflavone) is a natural substance found in apples, onions, tea and red wine (like resveratrol, it is derived from grape skins). Quercetin has been shown to be an antioxidant. Cai et al., 1999, *Free Radical Biol. Med.* 27: 822-829. Quercetin has been shown to be an efficacious agent for preventing and treating prostate cancer by workers at the Mayo Clinic. Xing et al., American Association for Cancer Research, $26^{th}$ Annual Meeting, Mar. 26, 2001. Prostate cancer is the second leading cause of death in men, with 31,500 fatalities and 200,000 diagnoses per year. Quercetin is currently in therapeutic use for treating inflammatory diseases and disorders.

A major goal in the pharmacological arts has been the development of reagents and methods that reduce the necessity of administering therapeutic compounds, drugs and other agents invasively (i.e., such as by injection). Most preferably, it has been a consistent goal in the art to develop therapeutic compounds, drugs and agents and formulations thereof that permit oral administration (see, for example U.S. Pat. No. 4,963,526 to Ecanow issued Oct. 16, 1990), although other reduced-invasiveness formulations such as suppositories have also been developed. Among the various routes of drug administration, the oral intake of drugs is undoubtedly preferred because of its versatility, safety and patient comfort.

In addition, it has been a goal in the nutritional arts to develop preparations that increase transit of certain nutrients through the gastrointestinal tract to increase uptake and delivery of such nutrients into the bloodstream. In particular, such preparations have been developed to permit chemically-labile nutrients (such as vitamins and other sensitive compounds) to pass through the chemically-hostile environment of the stomach for absorption in the intestines (see, for example, U.S. Pat. No. 5,958,450 to Tashiro issued Sep. 28, 1999). Preparations having enhanced intestinal uptake have also been deemed desirable.

One approach known in the prior art for improving efficiency of delivery of therapeutic compounds, drugs and other agents has been to envelop such compounds in a specialized lipid structure termed a liposome (see, for example, U.S. Pat. No. 4,744,989 to Payne et al. issued May 17, 1988). Liposomes generically comprise an enclosed lipid droplet having a core, typically an aqueous core, containing the compound. In certain embodiments, the compound is chemically conjugated to a lipid component of the liposome. In other embodiments, the compound is simply contained within the aqueous compartment inside the liposome.

Certain liposome formulations are known in the art.

U.S. Pat. No. 5,223,263, issued Jun. 29, 1993 to Hostetler et al. discloses conjugates between antiviral nucleoside analogues and polar lipids for inclusion in liposomes.

U.S. Pat. No. 5,466,468 to Schneider et al. issued Nov. 14, 1995 discloses parenterally administrable liposome formulations comprising synthetic lipids.

U.S. Pat. No. 5,484,809, issued Jan. 16, 1996 to Hostetler et al. discloses taxol and taxol derivatives conjugated to phospholipids.

U.S. Pat. No. 5,580,571, issued Dec. 3, 1996 to Hostetler et al. discloses nucleoside analogues conjugated to phospholipids.

U.S. Pat. No. 5,626,869 to Nyqvist et al. issued May 6, 1997 discloses pharmaceutical compositions wherein the pharmaceutically active compound is heparin or a fragment thereof contained in a defined lipid system comprising at least one amphiphatic and polar lipid component and at least one nonpolar lipid component.

U.S. Pat. No. 5,744,461, issued Apr. 28, 1998 to Hostetler et al. discloses nucleoside analogues conjugated to phosphonoacetic acid lipid derivatives.

U.S. Pat. No. 5,744,592, issued Apr. 28, 1998 to Hostetler et al. discloses nucleoside analogues conjugated to phospholipids.

U.S. Pat. No. 5,756,116, issued May 26, 1998 to Hostetler et al. discloses nucleoside analogues conjugated to phospholipids.

U.S. Pat. No. 5,843,509 to Calvo Salve et al. issued Dec. 1, 1998 discloses stabilization of colloidal systems through the formation of lipid-polysaccharide complexes comprising a water soluble and positively charged polysaccharide and a negatively charged phospholipid.

International Patent Application Publication Number WO89/02733, published April 1989 to Vical discloses conjugates between antiviral nucleoside analogues and polar lipids.

European Patent Application Publication Number 0350287A2 to Vical discloses conjugates between antiviral nucleoside analogues and polar lipids.

International Patent Application Publication Number WO93/00910 to Vical discloses conjugates between antiviral nucleoside analogues and polar lipids.

Rahman et al., 1982, Life Sci. 31: 2061-71 found that liposomes which contained galactolipid as part of the lipid appeared to have a higher affinity for parenchymal cells than liposomes which lacked galactolipid.

Gregoriadis, 1995, Trends in Biotechnology 13: 527-537 reviews the progress and problems associated with using liposomes for targeted drug delivery.

Ledley, 1995, Human Gene Therapy 6: 1129-1144 reviews the use of liposomes for gene therapy.

Mickisch, 1995, World J. Urology 13: 178-185 reviews the use of liposomes for gene therapy of renal cell carcinoma.

Yang et al. 1997, J. Neurotrauma 14: 281-297 review the use of cationic liposomes for gene therapy directed to the central nervous system.

Storm & Crommelin, 1997, Hybridoma 16: 119-125 review the preliminary use of liposomes for targeting chemotherapeutic drugs to tumor sites.

Manusama et al., 1998, Semin. Surg. Oncol. 14: 232-237 report on preclinical and clinical trials of liposome-encapsulated tumor necrosis factor for cancer treatments.

Although liposomes have conventionally been administered parenterally (see, for example, U.S. Pat. No. 5,466,468), reports of oral administration of liposome-related formulations have appeared in the art.

U.S. Pat. No. 4,921,757 to Wheatley et al. issued May 1, 1990 discloses controlled release of biologically active substances, such as drugs and hormones entrapped in liposomes that are protected from the biological environment by encapsulation within semi-permeable microcapsules or a permeable polymeric matrix.

U.S. Pat. No. 5,043,165 to Radhakrishnan to Aug. 27, 1991 disclosed a liposome composition for sustained release of steroidal drugs.

U.S. Pat. No. 5,762,904 to Okada et al. issued Jun. 9, 1998 discloses oral delivery of vaccines using polymerized liposomes.

U.S. Pat. No. 5,955,451 to Lichtenberger et al. issued Sep. 21, 1999 discloses compositions comprising non-steroid anti-inflammatory drugs (NSAID's) complexed with either zwitterionic or neutral phospholipids, or both, having reduced gastrointestinal irritating effects and enhanced antipyretic, analgesic, and anti-inflammatory activity.

Proliposomes are an alternative to conventional liposomal formulations. Proliposomes are dry, free-flowing granular products, which, on addition of water, disperse to form a multi-lamellar liposomal suspension. The stability problems associated with conventional liposomes such as aggregation, susceptibility to hydrolysis and/or oxidation are avoided by using proliposomes.

U.S. Pat. No. 5,635,206 to Ganter et al. discloses a process for preparing liposomes or proliposomes.

U.S. Pat No. 5,595,756 to Bally et al. discloses that the bioactive agent concentration in plasma increases when a synergistic effect is induced by lowering the pH (to approximately 2-3) of the solution in which a bioactive agent is entrapped within a liposome and including in the liposomal membrane an amine-bearing lipid.

U.S. Pat No. 6,093,406 to Alving et al. teaches liposomal derived vaccines that use a liposome and a compound that contains a net negative charge, a net positive charge (via stearylamine) or is neutral in conjunction with liposomes adsorbed to aluminum hydroxide.

Proliposomes of indomethacin were prepared using effervescent granules, which upon hydration yielded liposomes of high encapsulation efficiency and increased anti-inflammatory activity with decreased ulcerogenic index (see, for example, Katare et al., 1991, *J. Microencapsulation* 81: 1-7).

The proliposomal concept has been extended to administer drugs through various routes and also to the food industry wherein enzyme immobilization is essential for various food processing regimes. A typical example is the immobilization of the enzyme, chymotrypsin, in liposomes obtained from proliposomes.

There remains a need in the art for a general, inexpensive and effective means for delivering compounds such as polycyclic, aromatic, antioxidant or anti-inflammatory or anti-inflammatory compounds to an animal by oral administration. Advantageous embodiments of such delivery means are formulated to efficiently deliver such compounds to the appropriate portion of the gastrointestinal tract for efficient absorption.

SUMMARY OF THE INVENTION

The present invention is directed to an improved method for delivering polycyclic, aromatic, antioxidant or anti-inflammatory compounds to an animal by oral administration. This delivery system achieves specific delivery of such polycyclic, aromatic, antioxidant or anti-inflammatory compounds through associating the compounds with liposomes and proliposome components.

In preferred embodiments, the polycyclic, aromatic, antioxidant or anti-inflammatory inflammatory compound is formulated as a proliposomal composition that can be reconstituted in vivo to provide a liposomal preparation. Preferably, the invention provides pharmaceutical compositions comprising the polycyclic, aromatic, antioxidant or anti-inflammatory compound and a lipid formulated as a proliposomal preparation. In more preferred embodiments, the pharmaceutical compositions of the invention are formulated for oral administration. Most preferably, the pharmaceutical compositions of the invention formulated for oral administration comprise an enteric coating sufficient to prevent dissolution of the composition in the stomach of an animal. In alternative embodiments, the pharmaceutical compositions also comprise a protective coating between the enteric coating and the core of the composition comprising the proliposomal components thereof. Additional advantageous components of said orally-administrable pharmaceutical compositions further comprise the pharmaceutical compositions as will be understood by those with skill in the art.

Specific preferred embodiments of the present invention will become evident from the following more detailed description of certain preferred embodiments and the claims.

DETAILED DESCRIPTION OF THE PREFERRED EMBODIMENTS

The present invention provides compositions of matter and methods for facilitating the delivery of the polycyclic aromatic antioxidant or anti-inflammatory compounds to the tissues of an animal after oral administration. For the purposes of this invention, the term "polycyclic aromatic antioxidant or anti-inflammatory compound" is intended to encompass naturally-occurring, most preferably plant-derived, or synthetic compounds having antioxidant or anti-inflammatory properties and comprising cis-stilbene; trans-stilbene; 3-, 4-, or 4'-hydroxy, or (3,4')- or (4',5)-dihydroxy cis-stilbene; 3-, 4-, or 4'-hydroxy, or (3,4')- or (4',5)-dihydroxy trans-stilbene; carboxylated derivatives of cis-stilbene or trans-stilbene; halogenated derivatives of cis-stilbene or trans-stilbene; and resveratrol (trans-3,5,4'-trihydroxystilbene); or flavonoids, most preferably chrysin (5,7-dihydroxyflavone) or quercetin (3,3',4',5,7-pentahydroxyflavone), or biologically-active derivatives thereof.

Pharmaceutical compositions comprising the polycyclic aromatic antioxidant or anti-inflammatory compounds of the invention are preferably provided as proliposomal compositions that can be reconstituted, most preferably in vivo, to produce liposomal compositions of the polycyclic, aromatic, antioxidant or anti-inflammatory compounds.

As used herein, the term "proliposome" and "proliposomal" are intended to encompass calcium free, dry, free-flowing granular products, which, on addition of water, disperse to form multi-lamellar liposomal suspensions comprising the polycyclic, aromatic, antioxidant or anti-inflammatory compounds of the invention. The liposomes and preliposomes of the instant invention are not adsorbed to aluminum hydroxide. Advantageously, the stability problems associated with the conventional liposomes (such as aggregation, susceptibility to hydrolysis and oxidation) are avoided by using proliposomes.

The proliposomal compositions provided by the invention are reconstituted, particularly in vivo, to provide liposomal compositions wherein the polycyclic, aromatic, antioxidant or anti-inflammatory compounds of the invention are encapsulated in said liposomes. Even more preferably, the proliposomal composition is reconstituted in the intestines of the animal. When the proliposomes of the instant invention form liposomes in the intestines, the liposomes will be in an environment with a pH of approximately 6.4 (in humans.) This precludes the synergistic effect between the stearylamine and the biologically active component in a low pH (approximately 2-3) that is disclosed and claimed in U.S. Pat. No. 5,595,756.

In preparing the proliposomal compositions of the invention, lipid components including neutral lipids, positively-charged lipids or species, negatively-charged lipids or species, amphoteric lipids such as phospholipids, and cholesterol are advantageously used. As defined herein, the "lipid component" of the proliposomal compositions of the invention are intended to encompass a single species of lipid (such as a particular phospholipid) or combinations of such lipids, either of one type such as combinations of phospholipids (for example, a phosphatidylcholine plus a phosphatidylethanolamine) or of different types (such as a phospholipid plus a charged lipid, charged species, a neutral lipid or neutral species). Combinations comprising a multiplicity of different lipid types are also advantageously encompassed by the proliposomal compositions of the invention (see, Lehninger, 1975, *Biochemistry*, 2d ed., Chapters 11 & 24, Worth Publishers: New York; and Small, 1986, "From alkanes to phospholipids," *Handbook of Lipid Research: Physical Chemistry of Lipids,* Volume 4, Chapters 4 and 12, Plenum Press: New York).

Figure 4:
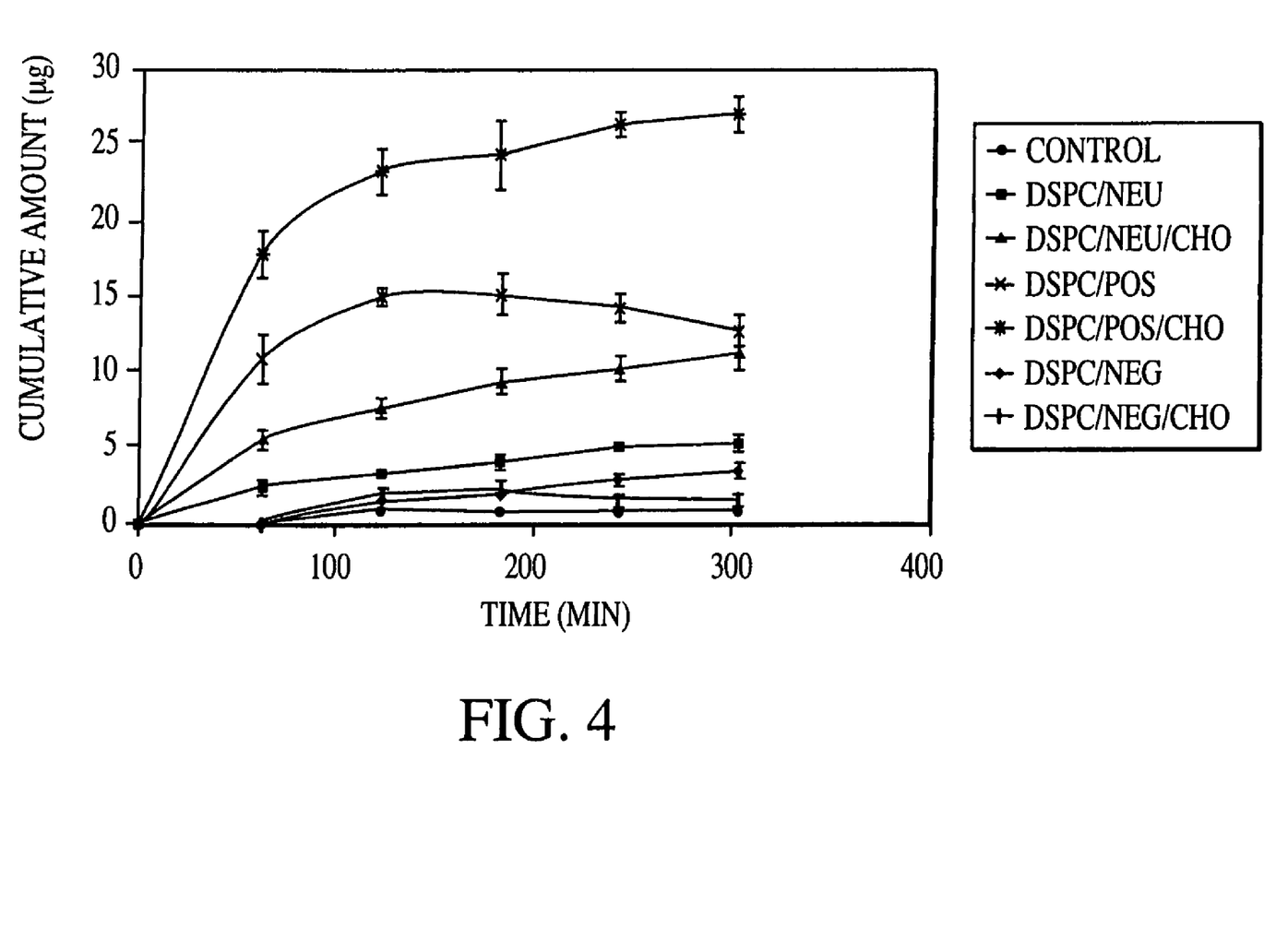
FIGS. 4 and 5 depict total accumulation of glyburide in the receiving chamber of a transwell comprising a Caco-2 cellular monolayer using the liposomal compositions of the invention, as set forth in Example 2.
Figure 5:
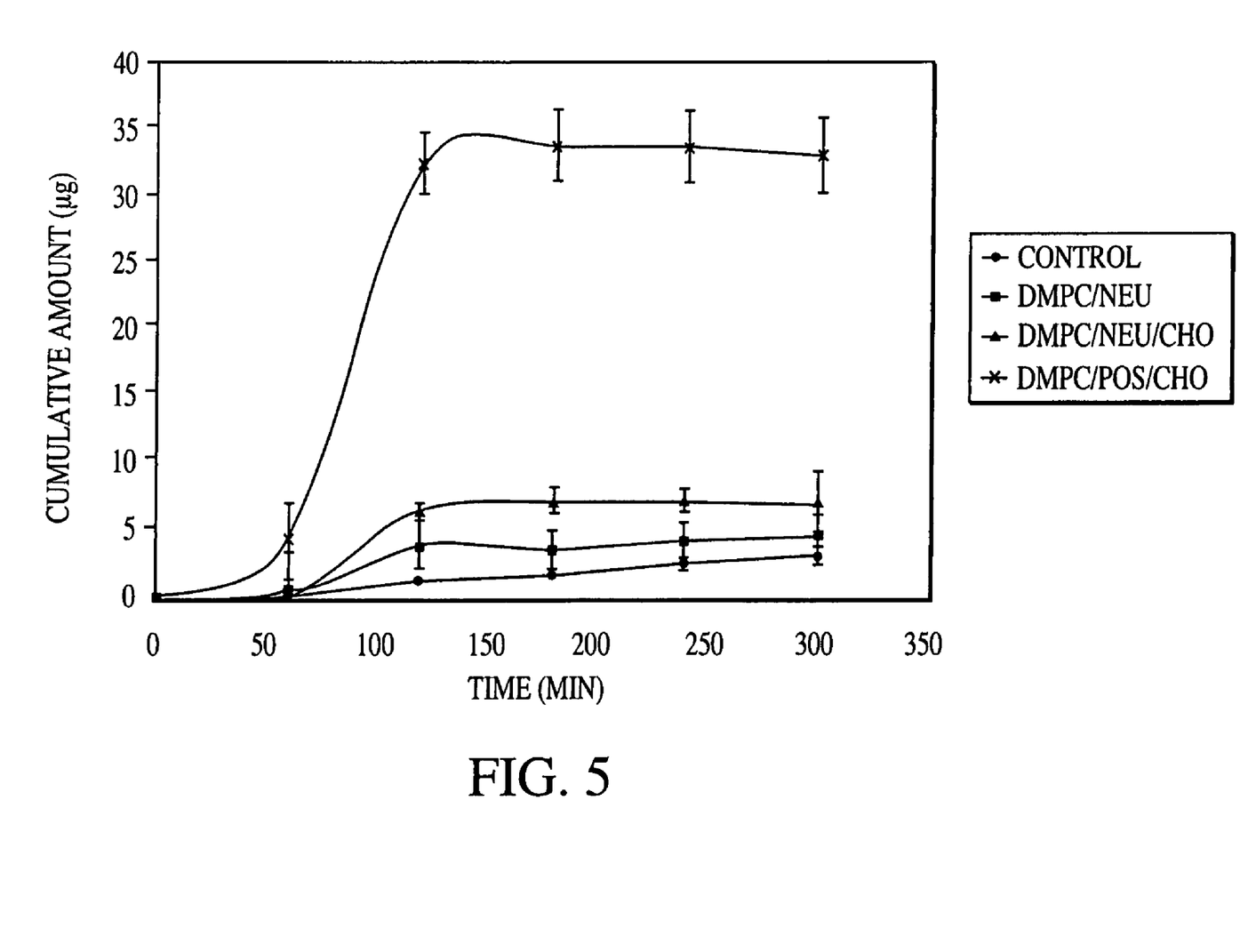

More preferably, the "lipid component" of the proliposomal compositions encompasses at least one lipid, and a positively charged species, that is not calcium. A preferred positively charged species is a primary aliphatic amine, such as stearylamine. More preferably, the lipid component also contains cholesterol. Most preferably, the lipid component consists essentially of one, two, or three independently selected lipids, a positively charged species and cholesterol. The lipids are independently a phosphatidylcholine, a phosphatidylethanolamine, sphingosine, or ceramide. More preferably, the phosphatidylcholine is distearylphosphatidylcholine, dimyristylphosphatidylcholine or a mixture thereof. Even more preferably, the phosphatidylcholine is distearylphosphatidylcholine or dimyristylphosphatidylcholine. It should also be noted that negatively charged species do not work; they decrease the biological availability of drugs in the present invention. See FIGS. 2 and 4.

Polycyclic, aromatic, antioxidant or anti-inflammatory compounds that are unstable in the stomach, or that show reduced absorption incident to transit through the stomach or other portions of the gastrointestinal tract, or polycyclic, aromatic, antioxidant or anti-inflammatory compounds that irritate the stomach, and those polycyclic, aromatic, antioxidant or anti-inflammatory compounds that are preferentially absorbed in the small intestine are preferred compounds useful with the liposomal formulations of the invention. In preferred embodiments, said compounds include but are not limited to cis-stilbene; trans-stilbene; 3-, 4-, or 4'-hydroxy, or (3,4')- or (4',5)-dihydroxy cis-stilbene; 3-4-, or 4'-hydroxy, or (3,4')- or (4',5)-dihydroxy trans-stilbene; carboxylated derivatives of cis-stilbene or trans-stilbene; halogenated derivatives of cis-stilbene or trans-stilbene; and resveratrol (trans-3,5,4'-trihydroxystilbene); or flavonoids, most preferably chrysin (5,7-dihydroxyflavone) or quercetin (3,3',4',5,7- pentahydroxyflavone), or biologically-active derivatives thereof.

The proliposomal preparations comprising the polycyclic, aromatic, antioxidant or anti-inflammatory compounds of the invention are preferably provided in a form that can be orally administered, including but not limited to syrups, elixirs, capsules, tablets, and emulsions. Preferred forms are tablets or capsules, most preferably comprising an enteric coating to prevent premature dissolution under the chemically harsh environment of the stomach. Enteric coatings are prepared as will be understood by one having skill in the art, and preferably include coatings including but not limited to eudragit and cellulose acetate phthalate.

In a preferred embodiment, the tablets or capsules of the invention comprise a protective coating between the enteric coating and the core of the capsule or tablet comprising the proliposomal preparations of the invention. In such embodiments, the protective coating is prepared as will be understood by one having skill in the art, and preferably include coatings including but not limited to hydroxypropyl methylcellulose, polyethylene glycol and ethylcellulose. In additional embodiments, the protective coating further comprises a plasticizing agent, including but not limited to triethylcitrate and polyvinyl pyrrolidone.

The tablets, capsules and other like embodiments of the proliposomal preparations and pharmaceutical compositions of the invention further advantageously comprise particle lubricants that minimize the tendency of the granular proliposomal compositions to agglomerate. By "particle lubricant" as used herein is meant the class of materials used in the manufacturing of pharmaceutical tablets as lubricants to improve the flowability and prevent agglomeration of an active agent during the tableting process. Examples of particle lubricants include talc, lactose, corn starch, ethyl cellulose, fatty acid salts such as magnesium stearate, agar pectin, fatty acids such as stearic acid, gelatin and acacia.

The invention specifically provides methods for preparing and administering the proliposomal compositions of the invention as disclosed in the Examples below, and pharmaceutical compositions comprising the proliposomal preparations of polycyclic, aromatic, antioxidant or anti-inflammatory compounds.

Animals to be treated with the proliposomal preparations and pharmaceutical compositions of the invention are intended to include all vertebrate animals, preferably domesticated animals, such as cattle, horses, goats, sheep, fowl, fish, household pets, and others, as well as wild animals, and most preferably humans.

One advantage of orally-administered liposomal formulations over parenterally-administered liposomal formulations is that oral administration reduces uptake of liposomes by the liver, thus reducing liver toxicity (which is a particular liability of parenterally-administered liposomal formulations). Oral formulations are targeted to deliver polycyclic, aromatic, antioxidant or anti-inflammatory compounds to the intestine, which is a large surface for absorption and results in slow release of the administered compound. Finally, oral administration avoids transport-mediated saturation of the polycyclic, aromatic, antioxidant or anti-inflammatory compounds of the invention.

The following Examples illustrate certain aspects of the above-described method and advantageous results. The following examples are shown by way of illustration and not by way of limitation.

EXAMPLE 1

Proliposomal formulations useful for oral administration were developed using an in vitro model system. Human Caco-2 cells (colon adenocarcinoma cells), grown on semipermeable filters, provide a simple and reliable in vitro model for studying drug transport across the intestinal mucosa. Caco-2 cells are recognized in the art for yielding useful predictions on oral absorption of new drug formulations.

1. Preparation of Proliposomal Formulations

In order to assay the proliposomal tablets of the invention, glyburide (glybenclamide), an oral blood-glucose-lowering drug of the sulfonylurea class, was used as model drug, because uptake in the CaCo-2 system can be monitored by measuring transport across monolayers formed by this cell line.

Proliposomal tablets were prepared as follows. The identities and amounts of each of the reagents used to prepare the tablets of the invention are shown in Table I. Phospholipids DMPC and DSPC were obtained from Avanti Polar Lipids (Alabaster, Ala.); glyburide, cholesterol, stearylamine, dicetylphosphate and all tissue culture reagents were obtained from Sigma Chemical Co. (St. Louis, Mo.); purified talc and anhydrous lactose were obtained from J. T. Baker (Phillipsburg, N.J.) and Quest, Int'l. (Hoffman Estates, Ill.); chloroform, methanol and ethanol were obtained from Fisher Scientific (Fairlawn, N.J.); Caco-2 cells were obtained from the American Type Culture Collection (Manassas, Va.; Accession No. HTB 37); and transwell culture chambers were obtained from Costar (Cambridge, Mass.).

Glyburide, lipid and cholesterol were dissolved at room temperature in 10 mL chloroform. Lactose (25 mg/tablet) was suspended in the organic mixture and the suspension evaporated to dryness at 60° C. in a conventional coating pan (pan drying method). The solid residue was collected and sifted through a #60 mesh screen. The sifted residue was then mixed with Explotab® (3 mg/tablet), lactose (50 mg/tablet) and talc (2 mg/tablet) and compressed into tablets using a Manesty B3B 16 station press. The tablets were then coated with a solution of hydroxypropyl methylcellulose in ethyl alcohol (3% w/v) containing triethyl citrate (15% of polymer weight) as a plasticizer. Eudragit L30 D-55 (7% w/w) was then applied on the coated tablets.

Table I provides a formulary for preparing proliposomal tablets according to the invention.

In alternative methods, proliposomal formulations can be prepared by lyophilization. In these embodiments, mixtures of lipids and drug are prepared in aqueous solution and then sonicated, causing small unilamellar liposomes to form and resulting in an optically-clear solution. Such a solution is then freeze-dried and mixed with the other components of the tablets as described above. This method has the advantages that it can be performed in five steps, and avoids the use of organic solvents, which can be toxic, in preparing the formulation.

TABLE I

Formulary for Preparing Proliposome Tablets

| Formulation | Quantity of each ingredient used (mg/tablet) | | | | | |
|---|---|---|---|---|---|---|
| | Glyburide | DSPC | DMPC | CHO | STA | DCP |
| DSPC/Neu | 5.0 | 10.0 | — | — | — | — |
| DSPC.Neu.Cho | 5.0 | 10.0 | — | 2.45 | — | — |
| DSPC/Pos | 5.0 | 10.0 | — | — | 0.35 | — |
| DSPC/Pos/Cho | 5.0 | 10.0 | — | 2.45 | 0.35 | — |
| DSPC/Neg | 5.0 | 10.0 | — | — | — | 0.69 |
| DSPC/Neg/Cho | 5.0 | 10.0 | — | 2.45 | — | 0.69 |
| DMPC/Neu | 5.0 | — | 10.0 | — | — | — |
| DMPC/Neu/Cho | 5.0 | — | 10.0 | 2.85 | — | — |
| DMPC/Pos/Cho | 5.0 | — | 10.0 | 2.85 | 0.40 | — |

DSPC = distearylphosphatidylcholine
DMPC = dimyristylphosphatidylcholine
STA = stearylamine (Pos: positively charged species)
CHO = cholesterol (Neu: neutral lipid)
DCP = dicetylphosphate (Neg: negatively charged species)

In other alternative methods, proliposomal formulations can be prepared by spray-drying. In these embodiments, mixtures of lipids and drug are prepared in aqueous solution. To such a mixture is added a surfactant such as Tween 80®, and then dried using a spray dryer. The resulting dried proliposomal preparation is mixed with the other components of the tablets as described above. This method has the advantages that it can be performed in five steps, is suitable for use with temperature-sensitive materials, and avoids the use of organic solvents, which can be toxic, in preparing the formulation.

In another embodiment of this alternative method, a mechanical mixer is used instead of using a surfactant. The mechanical mixer produces a proliposomal composition in the absence of a surfactant that can be spray-dried as described above. This embodiment is particularly advantageous because it avoids the use of both surfactants and organic solvents in preparing proliposomal formulations according to the invention.

2. Chemical Assays of Reagents and Proliposomal Formulations

The purity of the reagents used to make the proliposome tablets of the invention described herein was tested using differential scanning calorimetry. Samples were prepared by dissolving lipid with glyburide and cholesterol separately at a ratio of 1:1 (w/w) in an excess of chloroform. The organic layer was removed and thermograms obtained using a differential scanning calorimeter (TA Instruments, New Castle, Del., Model 2910). Each component was scanned both individually and using a mixture comprising glyburide, lipid and cholesterol at a ratio of 1:1:1 (w:w:w). 2-5 mg of sample was scanned at a rate of 20° C. per minute over a suitable temperature range (25-225° C.) in a hermetically-sealed aluminum pan. The peak transition temperatures of the dispersion were compared with the pure compounds. The results of these experiments are shown in FIGS. 1A through 1C.

Figure 1A:
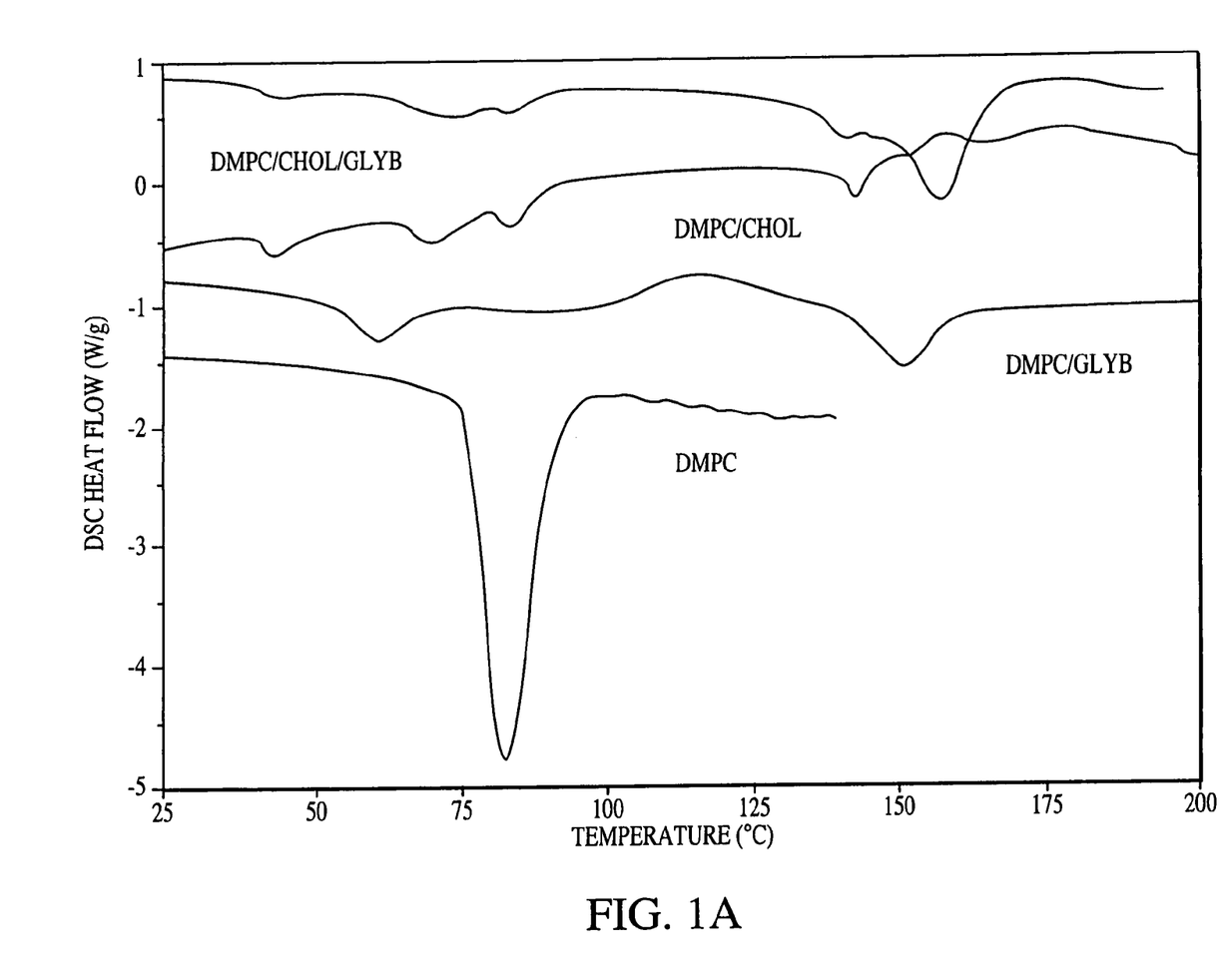
FIGS. 1A through 1C depict thermograms produced by differential scanning calorimetry as set forth in Example 1.

FIG. 1A shows a thermogram of DMPC alone compared with mixtures of DMPC and cholesterol (DMPC/CHOL), DMYC and glyburide (DNPC/GLYB) and DMPC, cholesterol, and glyburide (DMPC/CHOL/GLYB). Peak transition temperatures are shown in the Figure. In contrast to the simple and easily-recognizable peak transition temperature obtained for DMPC, the mixtures are heterogeneous, having more than one localized peak region where a thermal transition occurs.

Figure 1B:
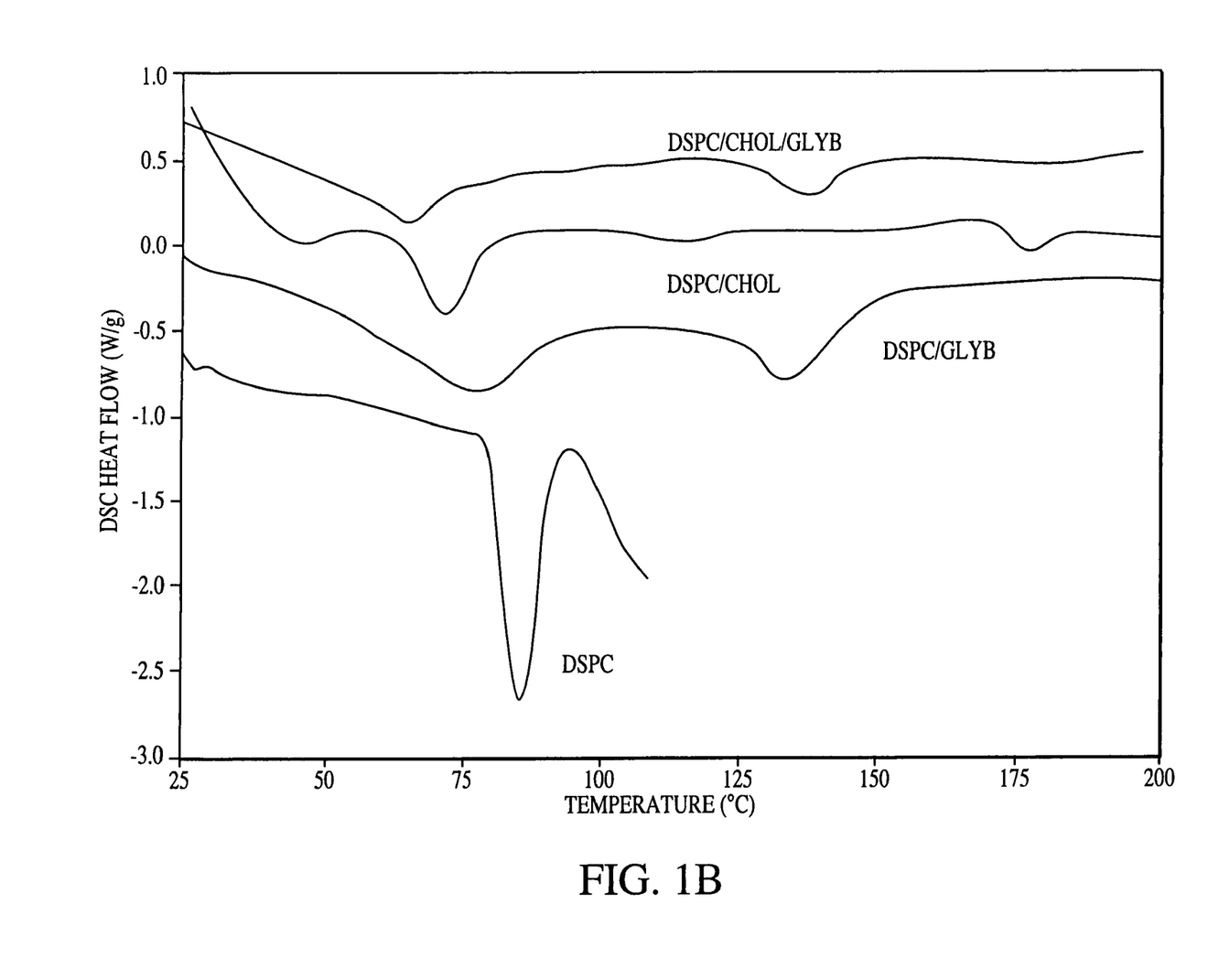

FIG. 1B shows a thermogram of DSPC alone compared with mixtures of DSPC and cholesterol (DSPC/CHOL), DSPC and glyburide (DMPC/GLYB) and DSPC, cholesterol and glyburide (DSPC/CHOL/GLYB). Peak transition temperatures are shown in the Figure. A similar pattern is observed herein, where there is a simple and easily-recognizable peak transition temperature obtained for DSPC, but the mixtures are heterogeneous, having more than one localized peak region where a thermal transition occurs.

Figure 1C:
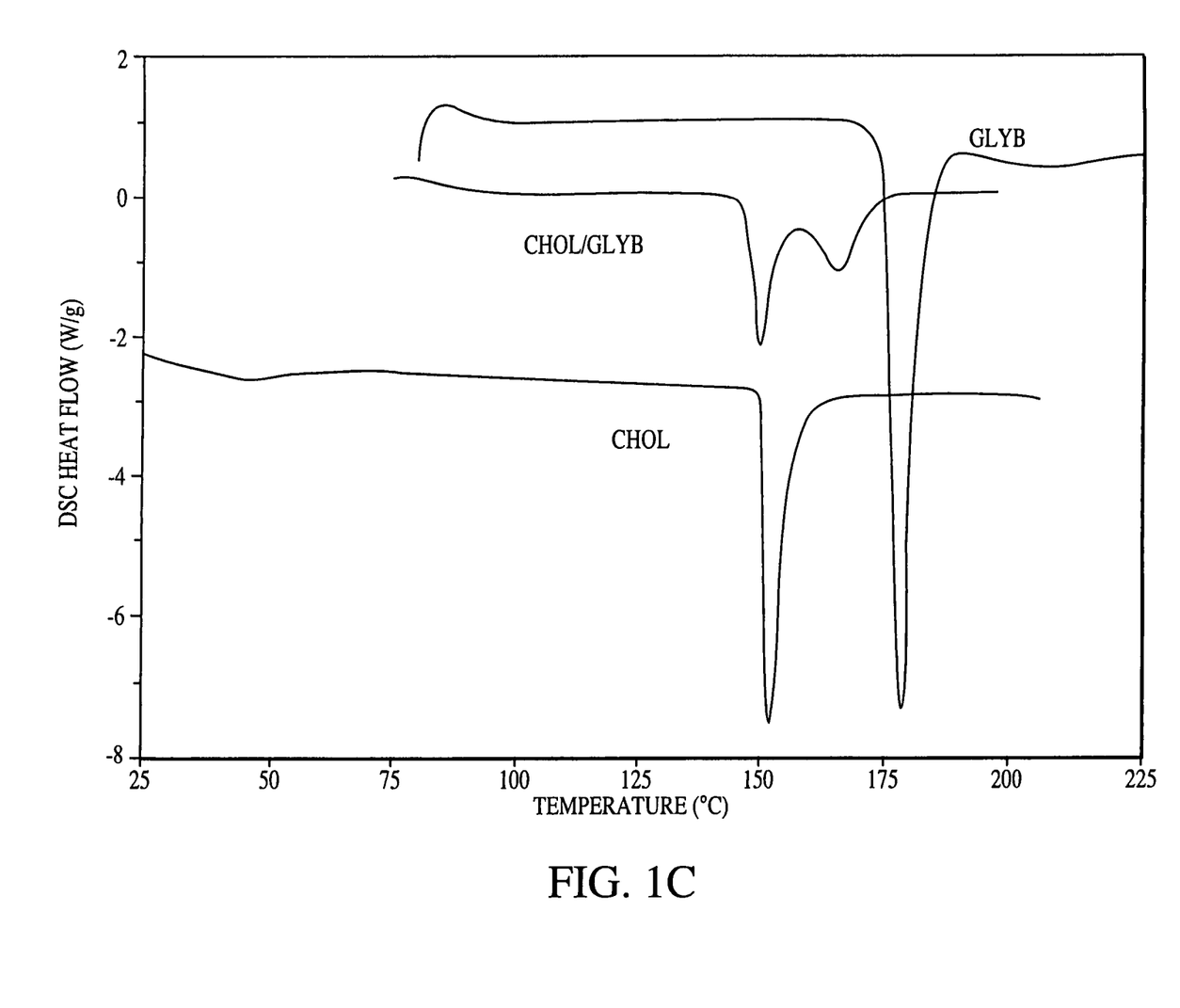

Thermograms were also obtained individually and in mixtures for glyburide and cholesterol, and these results are shown in FIG. 1C. From these thermograms, it is evident that the presence of cholesterol acts as an "impurity" in the drug, lowering its melting point The same effect is observed in mixtures of the drug and lipid. In the presence of both cholesterol and lipid, the melting point of glyburide is further decreased, demonstrating a synergistic effect. These results also indicate that the amount of heat required to melt the drug in a pure state is far higher than the amount needed when the drug is combined with cholesterol or lipid. This explains the increased solubility of the drag when prepared in a solid dispersion of lipid and/or cholesterol.

Liposomes were reconstituted from proliposomal tablets by adding one tablet to 1 mL phosphate buffered saline in a sterile glass vial. The tablet was allowed to stand at 37° C. for 1 hour with shaking, which was sufficient to dissolve the tablet and reconstitute the liposomal preparation.

Reconstituted liposomes were characterized for size distribution by large-angle dynamic light scattering using a particle size analyzer (Brookhaven Instruments, Model BI-90). Each preparation was diluted with filtered saline to an appropriate concentration to achieve a medium viscosity of 0.089 centipoise and a medium relative refractive index of 1.332 at room temperature. Measurements obtained under these condition are shown in Table II. These results indicated that the particle size of the resulting liposomes varied both with the presence or absence of cholesterol and with the identity of the phospholipid component. The mean diameter of the liposomes was greater in neutral liposome embodiments than in charged liposome embodiments, and can be explained by the greater propensity of neutral liposomes to aggregate or fuse with one another.

Encapsulation efficiency, defined as the percentage of the glyburide encapsulated in liposomes, was determined using the protamine-induced aggregations method as described in Kulkarni et al. (1995, *Pharm. Sci.* 1: 359-362). Briefly, each tablet was disintegrated in 1 mL of phosphate-buffered saline (PBS, pH 7.4) to give a concentration of 10 mg/mL of lipid. To 100 µL of the preparation, equal

TABLE II

Liposome Particle Size (nm) of Different Tablet Formulations

| Formulation/Charge | Lipid Type | |
| --- | --- | --- |
|  | DSPC | DMPC |
| Neutral | 1413 | 1825 |
| Neutral/Cholesterol | 1035 | 748 |
| Positive | 1059 | N.D. |
| Positive/Cholesterol | 867 | 629 |
| Negative | 3633 | N.D. |
| Negative/Cholesterol | 800 | N.D. |

N.D.: not determined quantities of a protamine solution (50 mg/mL) in PBS was added and vortexed for about 1 min. The mixture was then incubated for about 12 hours at room temperature. After incubation, the mixture was centrifuged at about 16,000×g for about 5 minutes. 100 µL of the supernatant was removed and the pellet was dissolved in about 1 mL of reagent-grade alcohol (95% ethanol) and sonicated for 5 minutes.

The quantity of glyburide in the pellet and the supernatant was determined by HPLC analysis using the Star® 9010 solvent system and Star 9095® variable-wavelength ultraviolet/visible spectrum spectrophotometric detector (Varian Associates, Walnut Creek, Calif.) and the data analyzed by a Dynamax® MacIntegrator (Rainin Instrument Co., Woburn, Mass.). HPLC analysis was performed using a C18 column (Phenominex®) packed with 5 µm particles and having dimensions of 250 mm in length and an internal diameter of 4.6 mm. The mobile phase was a solution of methanol in 0.1M phosphate buffer, pH 3.5 at a ratio of 75:25 by volume. Column flow rate was 1.0 ml/min and the output was scanned at a wavelength of 225 nm.

The results of these characterization experiments are shown in Table III.

These results demonstrated that a slightly higher percentage of the drug was encapsulated in DMPC. These results are consistent with a slightly higher amount of the drug being encapsulated in "fluid" liposomes (i.e., those comprising DMPC) than liposomes in a gel state (i.e., those comprising DSPC) at 37° C.

TABLE III

Drug Encapsulation Efficiency (% ± s.d.)

| Formulation | Lipid Type | |
| --- | --- | --- |
|  | DSPC | DMPC |
| Neutral | 81.6 ± 0.4 | 86.7 ± 2.7 |
| Neutral/Cholesterol | 80.4 ± 0.6 | 88.8 ± 1.2 |
| Positive | 78.4 ± 0.7 | N.D. |
| Positive/Cholesterol | 81.0 ± 1.2 | 87.6 ± 0.6 |

TABLE III-continued

Drug Encapsulation Efficiency (% ± s.d.)

| Formulation | Lipid Type | |
| --- | --- | --- |
|  | DSPC | DMPC |
| Negative | 81.2 ± 0.1 | N.D. |
| Negative/Cholesterol | 80.4 ± 0.4 | N.D. |

N.D.: Not determined

EXAMPLE 2

Caco-2 cell cultures were prepared as monolayers on polycarbonate transwells having a membrane pore size of 4 nm. Caco-2 cells were first grown in T-150 flasks (Falcon, Lincoln Park, N.J.) at 37° C. under an atmosphere of 5% $CO_2$ and 95% air in Dulbecco's modified Eagle's medium (pH 7.2, Sigma Chemical Co., St Louis, Mo.), with conventional supplements. The medium was changed every other day until the monolayers reached about 90% confluency. Media was removed and the cells were washed with Hank's balanced salt solution (HBSS, Sigma). The cells were trypsinized by adding 0.5 mL of a 0.25% trypsin solution containing 1 mM EDTA to each flask and incubating the monolayers for 10 min at 37° C. The separated cells were removed from the flasks and collected into centrige tubes, centriged at 200×g for 10 min, the supernatant removed and the pellet resuspended in a sufficient amount of Dulbecco's modified Eagle medium to yield a suspension that would produce about 60,000 cells/$cm^2$ on plating. The Caco-2 cells were then seeded into Transwell semipermeable membrane inserts having 4 µm pore size. In the transwells, media was changed every other day until the cells were used for the transport studies described below.

Caco-2 cell cultures on transwell membranes prepared as described above were used for transport studies about 17 days after plating. Proliposome tablets were dissolved as described above by incubation for 1 h with shaking at 37° C. in 2 mL HBSS. As a control, pure glyburide treated with chloroform was compressed into tablet form with lactose and Explotab®; all controls were treated exactly as experimental.

The medium from the transwell plates was gently removed using a micropipette. 0.5 mL of the reconstituted liposomal suspension was gently added to the donor compartment of the transwell and 1.5 mL of HBSS was added to the receiver compartment 100 µL of FITC-Dextran was then added to the donor compartment to a final concentration of 10 µg/mL of FITC-Dextran in the donor side. FITC-Dextran was used as a marker to test for the presence of leaks, if any, on the monolayers covering the semipermeable transwell membranes. Samples (300 µL) were carefully withdrawn from the receiver side at 50, 120, 180, 240, 300 minutes after addition, and the receiver side was replenished with 300 µL of fresh HBSS each time the sample was taken. Cells were incubated at 37° C. in a 5% $CO_2$/95% air atmosphere at all times during these assays. Sampling was done under aseptic conditions in a laminar air-flow hood.

The amount of glyburide transported during each sampling interval was determined by injecting 90 µL of the sample onto the HPLC system described above in Example 1 and peak areas were recorded. These experiments were performed in triplicate and the average of the results was reported. The results of the experiments are shown in FIGS. 2 through 5.

Figure 2:
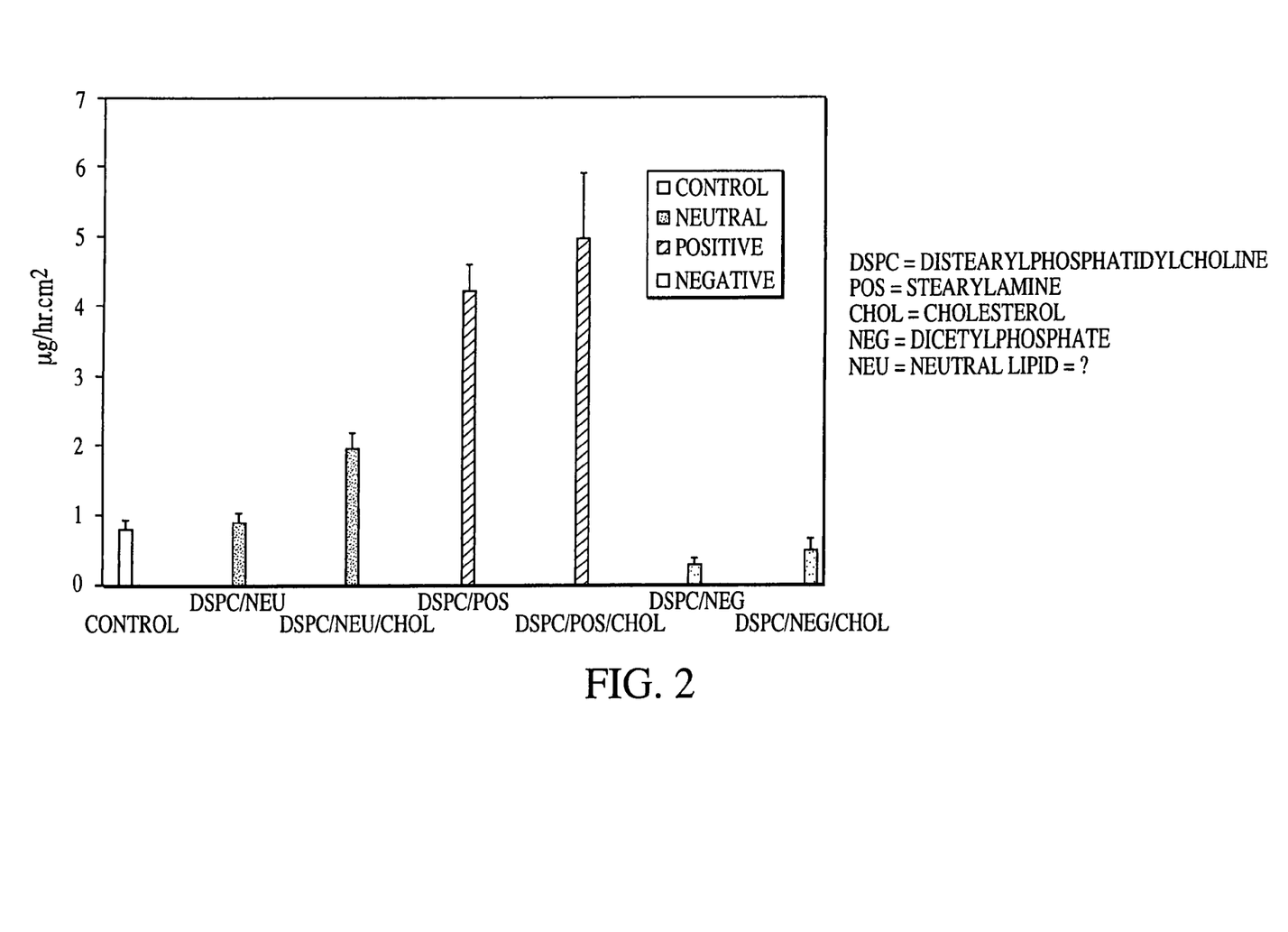
FIGS. 2 and 3 depict transfer rates of glyburide through a Caco-2 cellular monolayer using the liposomal compositions of the invention, as set forth in Example 2.
Figure 3:
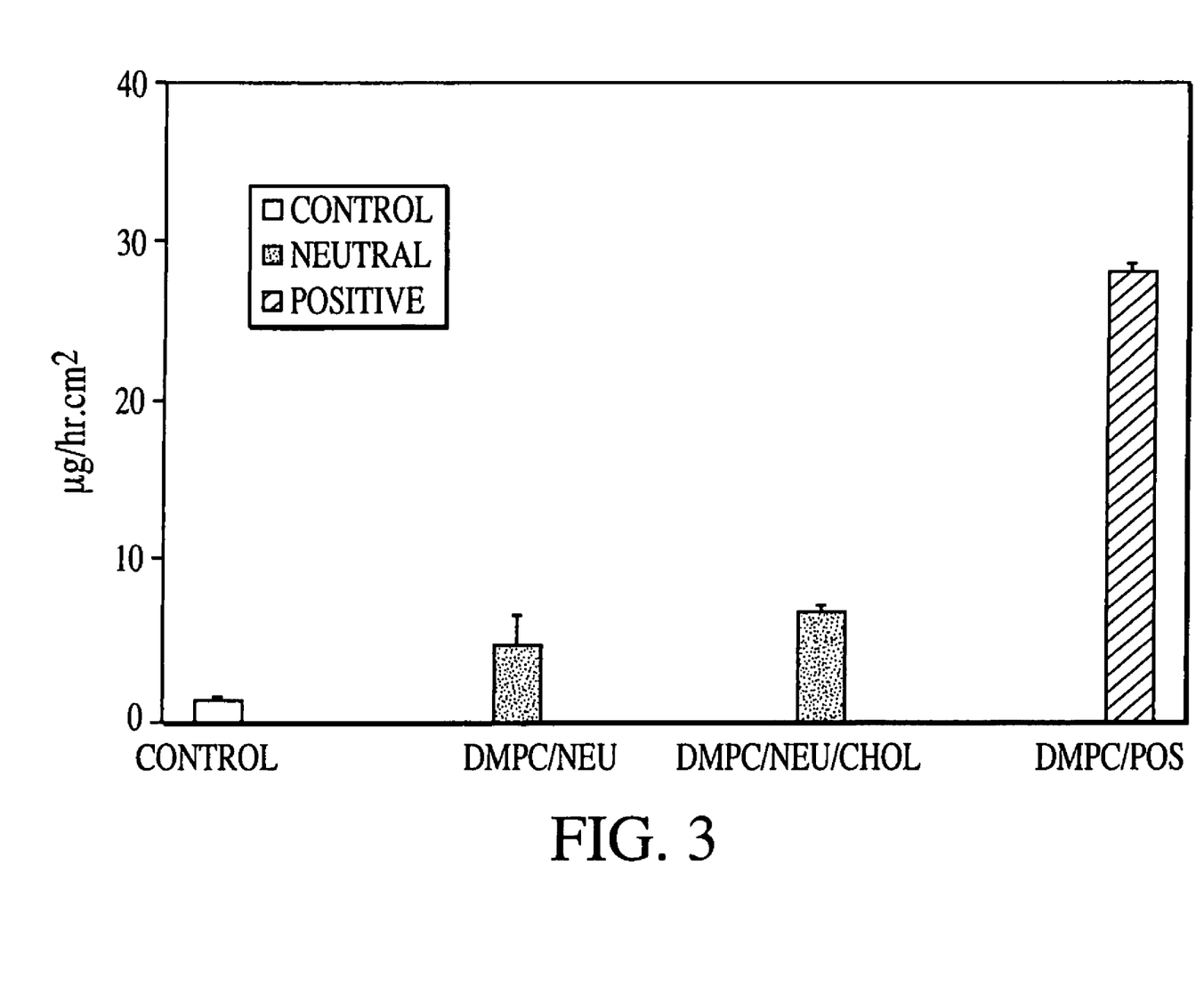

FIG. 2 shows the results of glyburide transit across Caco-2 cell monolayers in formulations containing distearylphosphatidylcholine (DSPC). Control experiments performed in the absence of DSPC had a flow rate of almost 1 µg/hr•cm$^2$. Formulations of glyburide with DSPC (a "neutral" lipid at physiological pH) showed a similar level of flux across the monolayer, although the addition of cholesterol to these formulations increased the flux about two-fold. Formulations of glyburide with negatively-charged lipid, on the other hand, in either the presence or absence of cholesterol were transported across the monolayer at a lower rate. In contrast, formulations of glyburide with positively-charged lipid were transported across the membranes at a rate about fourfold higher than control, and the addition of cholesterol increased this to a rate of about fivefold higher than control.

FIG. 3 shows the results of parallel experiments using dimyristylphosphatidylcholine (DMPC) as the lipid component. A similar pattern of glyburide flux was seen in these experiments; however, the degree of enhancement of transit across the Caco-2 cell monolayer was much higher for formulations containing DMPC. For example, glyburide formulations containing DMPC and positively-charged lipid had a transit rate almost thirty-fold higher than control. Formulations of neutral lipid were elevated to a lesser degree; in the presence of cholesterol such formulations had a transit rate about eightfold higher than control, and in the absence of cholesterol this rate was about fivefold higher than control.

FIGS. 4 and 5 show the cumulative amount of transported glyburide using DSPC- and DMPC-containing formulations over a five hour period. FIG. 4 shows DSPC-containing formulations, wherein the highest accumulation levels were achieve with glyburide formulations containing DSPC and positively-charged lipid (about 27 μg). Similar formulations additionally containing cholesterol had lower total amounts (about 13 μg). DSPC formulations containing neutral lipid and cholesterol showed slower kinetics but achieved essentially the same total accumulation as DSPC/positive lipid/cholesterol formulations. Formulations containing DSPC and neutral lipids in the absence of cholesterol showed the same total accumulation as control (about 2.5 μg), while DSPC formulations with negatively-charged lipid (in the presence or absence of cholesterol) showed lower total accumulation amounts.

FIG. 5 shows the results of similar experiments performed with DMPC formulations. Total accumulation levels were noticeably higher than control only for formulations containing DMPC, positively-charged lipid and cholesterol (about 34 μg), while DMPC formulations with neutral lipid (in the presence or absence of cholesterol) resulted in total accumulation at levels equivalent to control (about 2-5 μg).

These results demonstrated that liposomes can be successfully prepared for oral administration in the form of enteric-coated proliposome tablets. The presence of cholesterol reduces the particle size of the formulation. Proliposomes provide a stable system of production of liposomes for oral administration. Degradation of proliposome contents of the tablet in the stomach can be effectively avoided by administering the proliposomes as enteric-coated tablets. Enhanced transport of glyburide across Caco-2 cells was observed with such liposomal formulations. Although the transport of glyburide with DMPC formulations is higher than transport in the DSPC formulation in vitro, DSPC formulations are better suited for in vivo conditions because of the rigidity and increased stability of the membrane against the attack of bile salts and enzymes of the intestine.

Since in vitro transport across Caco-2 cells is an indication of bioavailability, an increased transport with the liposome formulation suggests an increased bioavailabilty of compounds that are poorly absorbed otherwise. For example, using a suitable polymer coating for the proliposomal tablets of the invention, colonic delivery of drugs, especially peptides may be possible.

Proliposomes are ideally suited for lipophilic compounds, since the majority of such a polycyclic, aromatic, antioxidant or anti-inflammatory compound will partition into the lipid phase. These results also have implications for developing formulations that stabilize the encapsulated drug.

It should be understood that the foregoing disclosure emphasizes certain specific embodiments of the invention and that all modifications or alternatives equivalent thereto are within the spirit and scope of the invention as set forth in the appended claims.

What is claimed is:

1. A pharmacological composition in a tablet or capsule comprising a proliposomal preparation, an enteric coating, and a protective coating in between the proliposomal preparation and the enteric coating, wherein the proliposomal preparation consists of at least one phospholipid, stearylamine, cholesterol, a polycyclic aromatic antioxidant or anti-inflammatory compound, and an optional particle lubricant, where the weight amount of stearylamine is less than the weight amount of cholesterol, and where the weight amount of cholesterol is less than the weight amount of phospholipid.

2. A pharmacological composition according to claim 1 wherein the polycyclic aromatic antioxidant or anti-inflammatory compound is cis-stilbene; trans-stilbene; 3-, 4-, or 4'-hydroxy, or (3,4')- or (4',5)-dihydroxy cis-stilbene; 3-, 4-, or 4'-hydroxy, or (3,4')- or (4',5)-dihydroxy trans-stilbene; carboxylated derivatives of cis-stilbene or trans-stilbene; halogenated derivatives of cis-stilbene or trans-stilbene; resveratrol (trans-3,5,4'-trihydroxystilbene); chrysin (5,7-dihydroxyflavone) or quercetin (3,3',4',5,7-pentahydroxyflavone), or biologically-active derivatives thereof.

3. A pharmacological composition according to claim 2 wherein the enteric coating is cellulose acetate phthalate or a poly(acrylate, methacrylate) copolymer.

4. A pharmacological composition according to claim 2 wherein the protective coating is hydroxypropyl methylcellulose, polyethylene glycol or ethylcellulose.

5. A pharmacological composition according to claim 1 wherein the protective coating further comprises a plasticizer.

6. A pharmacological composition according to claim 5 wherein the plasticizer is triethylcitrate or polyvinyl pyrrolidine.

7. A pharmacological composition according to claim 1 wherein the proliposomal composition consists of at least one phospholipid, stearylamine, cholesterol, a polycyclic aromatic antioxidant or anti-inflammatory compound, and a particle lubricant, wherein the particle lubricant is talc, lactose, corn starch, ethyl cellulose, fatty acids or salts thereof, agar, pectin, gelatin or acacia.

8. A pharmacological composition according to claim 2 wherein the polycyclic aromatic antioxidant or anti-inflammatory compound is resveratrol, quercetin or chrysin.

9. A pharmacological composition according to claim 1 wherein the phospholipid is a phosphatidylcholine, a phosphatidylethanolamine, sphingosine, ceramide, or a mixture thereof.

10. A pharmacological composition according to claim 9 wherein the phosphatidylcholine is distearylphosphatidylcholine, dimyristylphosphatidylcholine or a mixture thereof.

11. A method for increasing the bioavailability of a polycyclic, aromatic antioxidant or anti-inflammatory compound, said method comprising orally administering to an animal in need thereof a pharmaceutical preparation in a capsule or tablet comprising a proliposomal preparation, an enteric coating, and a protective coating in between the proliposomal preparation and the enteric coating, wherein the proliposomal preparation consists of at least one phospholipid, stearylamine, cholesterol, a polycyclic, aromatic antioxidant or anti-inflammatory compound, and an optional particle lubricant, where the weight amount of stearylamine is less than the weight amount of cholesterol, and where the weight amount of cholesterol is less than the weight amount of phospholipid.

12. A method according to claim 11 wherein the animal is a human.

13. A method according to claim 11 wherein the polycyclic aromatic antioxidant or anti-inflammatory compound is cis-stilbene; trans-stilbene; 3-, 4-, or 4'-hydroxy, or (3,4')- or (4',5)-dihydroxy cis-stilbene; 3-, 4-, or 4'-hydroxy, or (3,4')- or (4',5)-dihydroxy trans-stilbene; carboxylated derivatives of cis-stilbene or trans-stilbene; halogenated derivatives of cis-stilbene or trans-stilbene; resveratrol (trans-3,5,4'-trihydroxystilbene); chrysin (5,7-dibydroxyflavone) or quercetin (3,3',4',5,7-pentahydroxyflavone), or biologically-active derivatives thereof.

14. A method according to claim 13 wherein the polycyclic aromatic antioxidant or anti-inflammatory compound is resveratrol, quercetin or chrysin.

15. A method according to claim 11 wherein the enteric coating is cellulose acetate phthalate or a poly (acrylate, ruethacrylate) copolymer.

16. A method according to claim 11 wherein the protective coating is hydroxypropyl methylcellulose, polyethylene glycol or ethylcellulose.

17. A method according to claim 11 wherein the protective coating further comprises a plasticizer.

18. A method according to claim 17 wherein the plasticizer is triethylcitrate or polyvinyl pyrrolidine.

19. A method according to claim 11 wherein the proliposomal preparation consists of at least one phospholipid, stearylamine, cholesterol, a polycyclic, aromatic antioxidant or anti-inflammatory compound, and a particle lubricant, wherein
the particle lubricant is talc, lactose, corn starch, ethyl cellulose, fatty acids or salts thereof, agar, pectin, gelatin or acacia.

20. A method according to claim 11 wherein the phospholipid a phosphatidylcholine, a phosphatidylethanolamine, sphingosine, ceramide, or a mixtures thereof.

21. A method according to claim 20 wherein the phosphatidylcholine is distearylphosphatidylcholine, dimyristylphosphatidylcholine or a mixture thereof.

22. A method of preventing coronary heart disease, myocardial infarction, ischemia, stroke, thrombosis, pulmonary embolism, or cancer, said method comprising administering a composition of claim 1 to human in need thereof.

23. A method for delivering a polycyclic, aromatic, antioxidant or anti-inflammatory compound to the intestine or colon, said method comprising orally administering to an animal in need thereof a pharmaceutical preparation in a tablet comprising a proliposomal preparation, an enteric coating, and a protective coating in between the proliposomal preparation and the enteric coating, wherein the proliposomal preparation consists of at least one phospholipid, stearylamine, cholesterol, a polycyclic, aromatic, antioxidant or anti-inflammatory compound, and an optional particle lubricant, where the weight amount of stearylamine is less than the weight amount of cholesterol, and where the weight amount of cholesterol is less than the weight amount of phospholipid.

24. A method according to claim 23 wherein the animal is a human.

25. A method according to claim 23 wherein the polycyclic aromatic antioxidant or anti-inflammatory compound is cis-stilbene; trans-stilbene; 3-, 4-, or 4'-hydroxy, or (3,4')-or (4',5)-dihydroxy cis-stilbene; 3-, 4-, or 4'-hydroxy, or (3,4')- or (4',5)-dihydroxy trans-stilbene; carboxylated derivatives of cis-stilbene or trans-stilbene; halogenated derivatives of cis-stilbene or trans-stilbene; resveratrol (trans-3,5,4'-trihydroxystilbene); chrysin (5,7-dihydroxyflavone) or quercetin (3,3',4',5,7-pentahydroxyflavone), or biologically-active derivatives thereof.

26. A method according to claim 25 wherein the polycyclic aromatic antioxidant or anti-inflammatory compound is resveratrol, quercetin or chrysin.

27. A method according to claim 23 wherein the enteric coating is cellulose acetate phthalate or a poly(acrylate, methacrylate) copolymer.

28. A method according to claim 23 wherein the protective coating is hydroxypropyl methylcellulose, polyethylene glycol or ethylcellulose.

29. A method according to claim 23 wherein the protective coating further comprises a plasticizer.

30. A method according to claim 23 wherein the plasticizer is triethylcitrate or polyvinyl pyrrolidine.

31. A method according to claim 23 wherein the proliposomal preparation consists of at least one phospholipid, stearylamine, cholesterol, a polycyclic, aromatic, antioxidant or anti-inflammatory compound, and a particle lubricant, wherein the particle lubricant is talc, lactose, corn starch, ethyl cellulose, fatty acids or salts thereof, agar, pectin, gelatin or acacia.

32. A method according to claim 23 wherein the phospholipid is a phosphatidylcholine, a phosphatidylethanolamine, sphingosine, ceramide, or a mixture thereof.

33. A method according to claim 23 wherein the phosphatidylcholine is distearylphosphatidylcholine, dimyristylphosphatidylcholine or a mixture thereof.

* * * * *